US006197788B1

(12) United States Patent
Fletcher et al.

(10) Patent No.: US 6,197,788 B1
(45) Date of Patent: Mar. 6, 2001

(54) (−)-MEFLOQUINE TO BLOCK PURINGERGIC RECEPTORS AND TO TREAT MOVEMENT OR NEURODEGENERATIVE DISORDERS

(75) Inventors: Allan Fletcher, Cleveland; Lars Jacob Stray Knutsen, Berkshire; Richard H. P. Porter, Buckinghamshire; Scott Murray Weiss, Berkshire; Robin Shepherd, deceased, late of Berkshire, all of (GB), by Joy Miriam Shepherd, legal representative

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 09/355,205

(22) PCT Filed: Nov. 26, 1998

(86) PCT No.: PCT/GB98/03536

§ 371 Date: Sep. 27, 1999

§ 102(e) Date: Sep. 27, 1999

(87) PCT Pub. No.: WO99/26627

PCT Pub. Date: Jun. 3, 1999

(30) Foreign Application Priority Data

Nov. 26, 1997 (GB) .................................. 9725049
Sep. 4, 1998 (GB) .................................. 9819385

(51) Int. Cl.$^7$ .................................. A61K 31/47
(52) U.S. Cl. .................................. 514/314
(58) Field of Search .................................. 514/314

(56) References Cited

U.S. PATENT DOCUMENTS

| 3,536,809 | 10/1970 | Applezweig | 424/28 |
|---|---|---|---|
| 3,598,123 | 8/1971 | Zaffaroni | 126/268 |
| 3,630,200 | 12/1971 | Higuchi | 128/260 |
| 3,845,770 | 11/1974 | Theeuwes et al. | 128/260 |
| 3,916,899 | 11/1975 | Theeuwes et al. | 128/260 |
| 4,008,719 | 2/1977 | Theeuwes et al. | 128/268 |
| 4,327,215 | 4/1982 | Hickmann et al. | 546/176 |
| 4,687,660 | 8/1987 | Baker et al. | 424/465 |
| 4,769,027 | 9/1988 | Baker et al. | 424/493 |

FOREIGN PATENT DOCUMENTS

WO 98/39003 * 9/1998 (WO) .

OTHER PUBLICATIONS

Emery et al., Life Sci., vol. 33, No. 13, pp. 1285–1294, 1983.*
Litman et al., Biochim. Biophys. Acta, vol. 1361, No. 2, pp. 159–163, 1997.*
Besser et al., Nervenarzt, vol. 62, No. 12, pp. 760–761, 1991.*
Ngiam et al., Chem. Pharm. Bull., vol. 35, No. 1, pp. 409–412, 1987.*

Goodman–Gilman et al., The Pharmacological basis of therapeutics, Macmillan Publishing Co., New York, USA., pp. 125–127, 1987.*
Emery, C.E., et al., "Life Science, vol. 33. No. 13", *Arylmethanol and Thiosemiccarbazone Influence on Plasmodial Macromolecular Synthesis and Cell Stability*, pp. 1285–1294, (Jul. 15, 1983).
Litman, T. et al., "Biochemica et Biophysica Acta, vol. 1361", *Structure–activity relationships of P–glycoprotien interacting drugs: kinetic characterization of their effects on ATPase activity*, pp. 159–168, (1997).
Ngim, T.L., "Chem. Pharm. Bull., vol. 35 No. 1",*Sterospecific Inhibition of Cholinesterases by Mefloquine Enantiomers*, pp. 409–412, (1987).
Goodman–Gilman et al., "The Pharmacological Basis of Therapeutics", MacMillan Publishing Company, New York, *Therapeutic Uses of Anticholinesterase Drugs*, XP002093901, pp. 125–127, (1987).
Carrol, F.I. et al., "Journal of Medicinal Chemistry, vol. 17 No. 2", *Optical Isomers of Aryl–2–piperidylmenthanol Antimalarial Agents, Preparation, Optical Purity, and Absolute Sterochemistry*, pp. 210–219, (1974).
Thiesen, P.D., et al., "J. Org. Chem., 53",*Improved Procedure for Preparation of Optically Active 3–Hydroxyglutarate Monoesters and 3–Hydroxy–5–oxoalkanoic Acids*, pp. 2374–2379, (1988).
Shimada, Junichi et al., "Biooragnic & Medicinal Chemistry Letters, vol. 7 No. 18", *Adenosine $A_{2A}$ Antagonist with Potent Anti–Cataleptic Activity*, pp. 2349–2353, (1997).
Poucher, S.M., et al., "British Journal of Pharmacology, 115", *The in vitro Pharmacology of ZM 241385. a Potent, Non–Xanthine$A_{2A}$ Selective Adenosine Receptor Antagonist*, pp. 1096–1102, (1995).
WHO Scientific Group, "The WHO Technical Report", *Pratical Chemotherapy of Malaria*, pp. 1–145, (1990).
Basco, L.K. "Br. J. Clin Pharmac. 33", *In vitro Activity of the Enantiomers of Mefloquin, Halofantrine and Enpiroline against Plasmodium Falciparum*,pp. 517–520, (1990).
Palmer, K.J., "Drugs 45(3)"*Mefloquine: a Review of its Antimalarial Activity Pharmacokinetic Properties and Therapeutics Efficacy*pp. 430–475, (1993).
Ohnmacht, C.J. et al., "Journal of Medicinal Chemistry vol. 14 No. 10", *Antimalarials. 7. Bis(trifluoromethyl)–a–(2–piperidyl)–4–quinolinemethanols*[1], pp. 926–929, (1971).

(List continued on next page.)

Primary Examiner—Raymond Henley, III
(74) Attorney, Agent, or Firm—Foley & Lardner

(57) ABSTRACT

The present invention relates to the use of (±)-R*,S*)-alpha-2-piperidnyl-2,8-bis(trifluoromethyl)-4-quinolinemthanol and in particular (−)-(11S,2'R)-alpha-2-piperidnyl-2,8-bis(trifluoromethyl)-4-quinolinemthanol in the treatment of disorders in which the reduction of purinergic neurotransmission could be beneficial. The invention relates in particular to adenosine receptors, and particularly adenosine A2a receptors and to the treatment of movement disorders such as Parkinson's disease.

25 Claims, 4 Drawing Sheets

OTHER PUBLICATIONS

"The Lancet" vol. 341, *Anaesthesia Emergence Delirium After Mefloquine Propphlaxis*, pp. 632–633 and pp. 326–327, (Mar. 6, 1993).

Barrett, PJ et al., "BMJ vol. 313", *Comparison of Adverse Events Associates with uses of Mefloquine and Combination of Chloroquine and Proguanil as Antimalarial Prophylaxis: Postal and Telephone Survey of Travelers*, pp. 525–528, (Aug. 31, 1996).

"The Medical Journal of Australia, vol. 161"pp. 452 and 453, (Oct. 3, 1994).

Sowunmi A., "Transaction of the Royal Society of Tropical Medicine and Hygiene, 87", *Neuropsychiatric Side Effects of Mefloquine in Africans*, pp. 462–463, (1993).

Hennequin, C. et al., "Arch Intern Med, vol. 154", *Severe Psychiatric Side Effects Observed During Prophylaxis and Treatment With Mefloquine*, pp. 2360–2362, (Oct. 24, 1994).

Speich, R. et al., "The New England Journal of Medicine, vol. 331 No. 1", *Central Anticholinergic Syndrome with the Antimalarial Drug Mefloquine*, pp. 57–58 (Jul. 7, 1994).

Ledent, C. et al., "Nature vol. 388", *Aggressiveness, Hypoalgesia and High Blood Pressure in Mice Lacking the Adenosine $A_{2A}$ Receptor*, pp. 674–679, (Aug. 14, 1997).

Knutsen, L.J.S. et al., "Adenosine and ATP in Epilepsy", *Adenosine and ATP in Epilipsy* pp. 423–447 (1997).

Jacobson, et al., "Purinocepetor and Agents and Antagonist", *Development of Selective Purinoceptor Agonist and Antagonist*, pp. 101–128, (1987).

Chu, N.S. et al., "Epilepsia, 22", *Caffine–and Aminophlline–Induced Seizures*, pp. 85–95, (1981).

Rudolph, K.A. et al., "Journal of Cerebral Blood Flow and Metabolism, 7", *Effect of Theophylline on Ischemically Induced Hippocampal Damage in Mongolian Gerbils: A Behavioral and Histopathological Study* pp. 74–81, (1987).

Pinder, R.M. et al., "Antimalarials. II", *Antimarials, II.$^{1a}a$–(2–Piperidy)–and a–(2–Pyridyl)–2–trifluoromethly–4–quinolinemethanols$^{1b}$*, pp. 266–269, (Mar 1968).

Hoffman–La Roche, "Tetrahedrom, vol. 47 No. 36", *A Straightforward and High Yielding Synthesis of Mefloquine–II*, pp. 7609–7615, (1991).

Karle, J.M., et al., *Plasmodium falciparum: Role of Absolute Sterochemistry in the Antimalarial Activity of Synthetic Amino Alcohol Antimalarial Agents*, pp. 345–351, (1993).

* cited by examiner

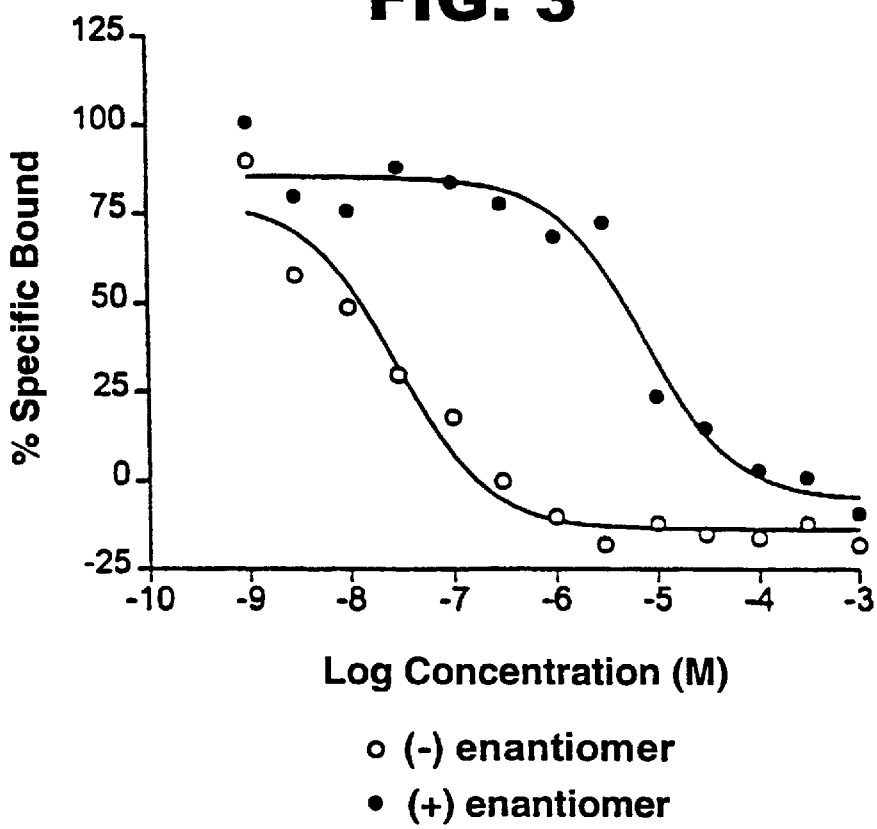
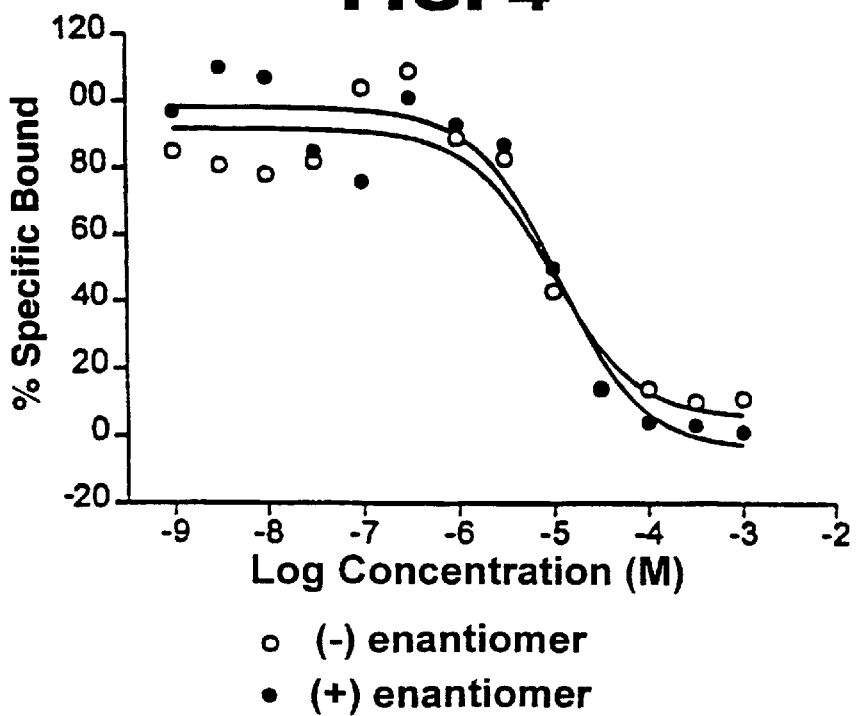

- Control (NECA)
- (+) enantiomer
- (-) enantiomer

(−)-MEFLOQUINE TO BLOCK PURINGERGIC RECEPTORS AND TO TREAT MOVEMENT OR NEURODEGENERATIVE DISORDERS

This is a 371 of PCT/GB98/03536 filed Nov. 26, 1998.

The present invention relates to the use of (±)-(R*,S*)-α-2-piperidinyl-2,8-bis(trifluoromethyl)-4-quinolinemethanol and in particular (−)-(11S,2'R)-α-2-piperidinyl-2,8-bis(trifluoromethyl)-4-quinolinemethanol in the treatment of disorders in which the reduction of purinergic neurotransmission could be beneficial. The invention relates in particular to adenosine receptors, and particularly adenosine $A_{2A}$ receptors, and to the treatment of movement disorders such as Parkinson's disease.

Movement disorders constitute a serious health problem, especially amongst the elderly sector of the population. These movement disorders are often the result of brain lesions. Disorders involving the basal ganglia which result in movement disorders include Parkinson's disease, Alzheimer's disease, Huntington's chorea and Wilson's disease. Furthermore, dyskinesias often arise as sequelae of cerebral ischaemia and other neurological disorders.

These are four classic symptoms of Parkinson's disease: tremor, rigidity, akinesia and postural changes. The disease is also commonly associated with depression, dementia and overall cognitive decline. Parkinson's disease has a prevalence of 1 per 1,000 of the total population. The incidence increases to 1 per 100 for those aged over 60 years. Degeneration of dopaminergic neurones in the substantia nigra and the subsequent reductions in interstitial concentrations of dopamine in the striatum are critical to the development of Parkinson's disease. Some 80% of cells from the substantia nigra need to be destroyed before the clinical symptoms of Parkinson's disease are manifested.

Current strategies for the treatment of Parkinson's disease are based on transmitter replacement therapy (L-dihydroxyphenylacetic acid (L-DOPA)), inhibition of monoamine oxidase (e.g. Deprenyl®), dopamine receptor agonists (e.g. bromocriptine and apomorphine) and antichloinergics (e.g. benztrophine, orphenadrine). Transmitter replacement therapy in particular does not provide consistent clinical benefit, especially after prolonged treatment when "on-off" symptoms develop, and this treatment has also been associated with involuntary movements of athetosis and chorea, nausea and vomiting. Despite new drug approvals, there is still a medical need in terms of improved therapies for movement disorders, especially Parkinson's disease. In particular effective treatments requiring less frequent dosing are required.

Blockade of $A_2$ adenosine receptors has recently been implicated in the treatment of movement disorders such as Parkinson's disease (Richardson, P. J. et al., Adenosine $A_{2A}$ receptor antagonists as new agents for the Treatment of Parkinson's disease. Trends Pharmacol. Sci. 1997, 18, 338–344) and in the treatment of cerebral ischaemia (Gao, Y. and Phillis, J. W., CGS 15943, an adenosine $A_2$ receptor antagonist, reduces cerebral ischaemic injury in the Mongolian Gerbil., Life Sci. 1994, 55, 61–65).

Adenosine is a naturally occurring purine nucleoside which has a wide variety of well-documented regulatory functions and physiological effects. The central nervous system (CNS) effects of this endogenous nucleoside have attracted particular attention in drug discovery, owing to the therapeutic potential of purinergic agents in CNS disorders (Jacobson, K. A. et al., Adenosine Receptors: Pharmacology, Structure-Activity Relationships and Therapeutic Potential. J. Med. Chem. 1992, 35, 407–422). This therapeutic potential has resulted in considerable recent research endeavour within the field of adenosine receptor agonists and antagonists (Bhagwhat, S. S.; Williams, M. Recent Progress in Modulators of Purinergic Activity. Exp. Opin. Ther. Patents 1995, 5,547–558).

Adenosine receptors represent a subclass ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$ (Fredholm, B. B., et al., Nomenclature and Classification of Purinoceptors. Pharmacol. Rev. 1994, 46, 143–156). The adenosine receptors are present in the CNS (Fredholm, B. B., Adenosine receptors in the central nervous system. News Physiol. Sci., 1995, 10, 122–128).

The design of $P_1$ receptor-mediated agents has been reviewed (Jacobson, K. A., Suzuki, F., Recent developments in selective agonists and antagonists acting at purine and pyrimidine receptors. Drug Dev. Res., 1997, 39, 289–300; Baraldi, P. G. et al., Current developments of $A_{2A}$ adenosine receptor antagonists. Curr. Med. Chem. 1995, 2, 707–722), and such compounds are claimed to be useful in the treatment of cerebral ischemia or neurodegenerative disorders, such as Parkinson's disease (Williams, M. and Burnstock, G. Purinergic neurotransmission and neuromodulation: a historical perspective. Purinergic Approaches Exp. Ther. (1997), 3–26. Editor: Jacobson, Kenneth A.; Jarvis, Michael F. Publisher: Wiley-Liss, New York, N.Y.).

The pharmacology of adenosine $A_{2A}$ receptors has been reviewed (Ongini, E.; Fredholm, B. B. Pharmacology of adenosine $A_{2A}$ receptors. Trends Pharmacol. Sci. 1996, 17(10), 364–372). One potential underlying mechanism in the aforementioned treatment of movement disorders by the blockade of $A_2$ adenosine receptors is the evidence of a functional link between adenosine $A_{2A}$ receptors to dopamine $D_2$ receptors in the CNS. Some of the early studies (e.g. Ferre, S. et al., Stimulation of high-affinity adenosine $A_2$ receptors decreases the affinity of dopamine $D_2$ receptors in rat striatal membranes. Proc. Natl. Acad. Sci. U.S.A. 1991, 88, 7238–41) have been summarised in two more recent articles (Fuxe, K. et al., Evidence for the existence of antagonistic intramembrane adenosine $A_{2A}$/dopamine $D_2$ receptor interactions in the basal ganglia: Analysis from the network to the molecular level. Adenosine Adenine Nucleotides Mol. Biol. Integr. Physiol., [Proc. Int. Symp.], 5th (1995), 499–507. Editors: Belardinelli, Luiz; Pelleg, Amir. Publisher: Kluwer, Boston, Mass.; Ferre, S. et al., Adenosine-dopamine receptor-receptor interactions as an integrative mechanism in the basal ganglia. Trends Neurosci. 1997, 20, 482–487).

As a result of these investigations into the functional role of adenosine $A_{2A}$ receptors in the CNS, especially in vivo studies linking $A_2$ receptors with catalepsy (Ferre et al., Stimulation of adenosine $A_2$ receptors induces catalepsy. Neurosci. Lett. 1991, 130, 162–4; Mandhane, S. N. et al., Adenosine $A_2$ receptors modulate haloperidol-induced catalepsy in rats. Eur. J. Pharmacol. 1997, 328, 135–141) investigations have been made into agents which selectively bind to adenosine $A_{2A}$ receptors as potentially effective treatments for Parkinson's disease.

While many of the potential drugs for treatment of Parkinson's disease have shown benefit in the treatment of movement disorders, an advantage of adenosine $A_{2A}$ antagonist therapy is that the underlying neurodegenerative disorder is also treated. The neuroprotective effect of adenosine $A_{2A}$ antagonists has been reviewed (Ongini, E.; Adami, M.;

Ferri, C.; Bertorelli, R., Adenosine $A_{2A}$ receptors and neuroprotection. *Ann. N.Y. Acad. Sci.* 1997, 825 (Neuroprotective Agents), 30–48).

Xanthine derivatives have been disclosed as adenosine $A_2$ receptor antagonists as useful for treating various diseases caused by hyperfunctioning of adenosine $A_2$ receptors, such as Parkinson's disease (see, for example, EP-A-565377).

One prominent xanthine-derived adenosine $A_{2A}$ selective antagonist is CSC [8-(3-chlorostyryl)caffeine] (Jacobson et al., CSC 8-(3-chlorostyryl)caffeine (CSC) is a selective $A_2$-adenosine antagonist in vitro and in vivo. *FEBS Lett.*, 1993, 323, 141–144). New non-xanthine structures sharing these pharmacological properties include SCH 58261 and its derivatives (Baraldi, P. G. et al., Pyrazolo[4,3-e]-1,2,4-triazolo[1,5-c]pyrimidine Derivatives: Potent and Selective $A_{2A}$ Adenosine Antagonists. *J. Med. Chem.* 1996, 39, 1164–71).

Theophylline, a bronchodilator drug which is a mixed antagonist at adenosine $A_1$ and $A_{2A}$ receptors, has been studied clinically. To determine whether a formulation of this adenosine receptor antagonist theophylline would be of value in Parkinson's disease an open trial was conducted on 15 Parkinsonian patients, treated for up to 12 weeks with a slow release oral theophylline preparation (150 mg/day), yielding serum theophylline levels of 4.44 mg/L after one week. The patients exhibited significant improvements in mean objective disability scores and 11 reported moderate or marked subjective improvement (Mally, J., Stone, T. W. The effect of theophylline on Parkinsonian symptoms, *J. Pharm. Pharmacol.* 1994, 46, 515–517).

KF 17837 [(E)-8-(3,4-dimethoxystyryl)-1,3-dipropyl-7-methylxanthine] is a selective adenosine $A_{2A}$ receptor antagonist which on oral administration significantly ameliorated the cataleptic responses induced by intracerebroventricular administration of an adenosine $A_{2A}$ receptor agonist, CGS 21680. KF 17837 also reduced the catalepsy induced by haloperidol and reserpine. Moreover, KF 17837 potentiated the anticataleptic effects of a subthreshold dose of L-DOPA plus benserazide, suggesting that KF 17837 is a centrally active adenosine $A_{2A}$ receptor antagonist and that the dopaminergic function of the nigrostriatal pathway is potentiated by adenosine $A_{2A}$ receptor antagonists (Kanda, T. et al., KF 17837: a novel selective adenosine $A_{2A}$ receptor antagonist with anticataleptic activity. *Eur. J. Pharmacol.* 1994, 256, 263–268). The structure activity relationship (SAR) of KF 17837 has been published (Shimada, J. et al., Adenosine $A_{2A}$ antagonists with potent anti-cataleptic activity. *Bioorg. Med. Chem. Lett.* 1997, 7, 2349–2352). Recent data has also been provided on the $A_{2A}$ antagonist KW-6002 (Kuwana, Y et al., $A_{2A}$ adenosine receptor antagonists are antiparkinsonian in animal models., *Soc. Neurosci. Abstr.* 1997, 23, 119.14; and Kanda, T. et al., Adenosine $A_{2A}$ antagonist: A novel antiparkinsonian agent that does not provoke dyskinesia in parkinsonian monkeys. *Ann. Neurol.* 1998, 43(4), 507–513).

The prominent adenosine $A_{2A}$ antagonist SCH 58261 (7-(2-phenylethyl)-5-amino-2-(2-furyl)-pyrazolo-[4,3-e]-1,2,4-triazolo[1,5-c] pyrimidine) (Baraldi, P. G. et al., Pyrazolo[4,3-e]-1,2,4-triazolo[1,5-c]pyrimidine Derivatives: Potent and Selective $A_{2A}$ Adenosine Antagonists. *J. Med. Chem.* 1996, 39, 1164–71) is reported as also having effect in the treatment of movement disorders (Ongini, E. SCH 58261: A selective $A_{2A}$ adenosine receptor antagonist. *Drug Dev. Res.* 1997, 42(2), 63–70) and has been followed up by a later series of compounds (Baraldi, P. G. et al., Design, Synthesis, and Biological Evaluation of a Second Generation of Pyrazolo[4,3-e]-1,2,4-triazolo[1,5-c] pyrimidines as Potent and Selective $A_{2A}$ Adenosine Receptor Antagonists. *J. Med. Chem.* 1998, 41(12), 2126–2133).

The foregoing discussion indicates that a potentially effective treatment for movement disorders in humans would comprise agents which act as antagonists at adenosine $A_{2A}$ receptors.

It has now been found that (−)-(11S,2′R)-α-2-piperidinyl-2,8-bis(trifluoromethyl)-4-quinolinemethanol exhibits unexpected antagonist binding affinity at the adenosine $A_{2A}$ receptor. (−)-(11S,2′R)-α-2-piperidinyl-2,8-bis(trifluoromethyl)-4-quinolinemethanol alone or in admixture with (+)-(11R,2′S)-α-2-piperidinyl-2,8-bis(trifluoromethyl)-4-quinolinemethanol, may therefore be a drug suitable for the treatment of movement disorders, such as disorders of the basal ganglia which result in dyskinesias. These may include Parkinson's disease, Alzheimer's disease, spasticity, Huntingdon's chorea and Wilson's disease.

It has been found that the use of (±)-(R*,S*)-α-2-piperidinyl-2,8-bis(trifluoromethyl)-4-quinolinemethanol, and in particular (−)-(11S,2′R)-α-2-piperidinyl-2,8-bis(trifluoromethyl)-4-quinolinemethanol, in the presence or absence of other drugs for treating Parkinson's disease can result in better control of symptoms of this disease.

(±)-(R*,S*)-α-2-piperidinyl-2,8-bis(trifluoromethyl)-4-quinolinemethanol, which consists of the individual enantiomers (+)-(11R,2′S)-α-2-piperidinyl-2,8-bis(trifluoromethyl)-4-quinolinemethanol and (−)-(11S,2′R)-α-2-piperidinyl-2,8-bis(trifluoromethyl)-4-quinolinemethanol, is marketed as a racemic mixture as Mefloquine (Lariam®), an effective and widely-used antimalarial agent.

In the present application, reference to (−)-(11S,2′R)-α-piperidinyl-2,8-bis(trifluoromethyl)-4-quinolinemethanol and (+)-(11R,2′S)-α-piperidinyl-2,8-bis(trifluoromethyl)-4-quinolinemethanol is reference to the compounds identified as having these structures and these absolute stereochemistries in Carroll and Blackwell, J. Med. Chem. 1974, 17, 210–219. The structures of the (+)-enantiomer and the (−)-enantiomer of α-2-piperidinyl-2,8-bis(trifluoromethyl)-4-quinolinemethanol are shown below.

(+)-enantiomer
(+)-(11R, 2′S)

(−)-enantiomer
(−)-(11S, 2′R)

In the event that the assignment of absolute stereochemistries by Carroll and Blackwell was incorrect, reference in the present application to the (−)-(11S,2′R) and (+)-(11R, 2′S) enantiomers shall be taken as reference to the compounds identified as such by Carroll and Blackwell and not as reference to the true absolute stereochemistries.

(−)-(11S,2′R)-α-2-piperidinyl-2,8-bis(trifluoromethyl)-4-quinolinemethanol is structurally unrelated to other adenosine receptor antagonists, and furthermore this agent possesses a long half life (345 h, 95% Cl) following doses of 250 mg per week (Hellgren, U. et al., Enantioselective pharmacokinetics of mefloquine during long-term intake of the prophylactic dose *Br. J. Clin. Pharmacol.* 1997, 44, 119–124).

According to the present invention there is provided use of (−)-(11S,2'R)-α-2-piperidinyl-2,8-bis(trifluoromethyl)-4-quinolinemethanol or a pharmaceutically acceptable salt thereof in the manufacture of a medicament for the treatment or prevention of a disorder in which the blocking of purine receptors, particularly adenosine receptors and more particularly $A_{2A}$ receptors, may be beneficial.

According to a further aspect of the present invention there is provided a method of treating or preventing a disorder in which the blocking of purine receptors, particularly adenosine receptors and more particularly $A_{2A}$ receptors, may be beneficial, the method comprising administration to a subject in need of such treatment an effective dose of (−)-(11S,2'R)-α-2-piperidinyl-2,8-bis(trifluoromethyl)-4-quinolinemethanol or a pharmaceutically acceptable salt thereof.

The disorder may be caused by the hyperfunctioning of the purine receptors.

According to a further aspect of the present invention there is provided use of (−)-(11S,2'R)-α-2-piperidinyl-2,8-bis(trifluoromethyl)-4-quinolinemethanol or a pharmaceutically acceptable salt thereof in the manufacture of a medicament for the treatment or prevention of movement disorders in a subject.

According to a further aspect of the invention there is provided a method of treating or preventing movement disorders comprising administration to a subject in need of such treatment an effective dose of (−)-(11S,2'R)-α-2-piperidinyl-2,8-bis(trifluoromethyl)-4-quinolinemethanol or a pharmaceutically acceptable salt thereof.

According to a further aspect of the invention there is provided use of (−)-(11S,2'R)-α-2-piperidinyl-2,8-bis(trifluoromethyl)-4-quinolinemethanol or a pharmaceutically acceptable salt thereof in the manufacture of a medicament for neuroprotection in a subject.

According to a further aspect of the invention there is provided a method of neuroprotection comprising administration to a subject in need of such treatment an effective dose of (−)-(11S,2'R)-α-2-piperidinyl-2,8-bis(trifluoromethyl)-4-quinolinemethanol or a pharmaceutically acceptable salt thereof.

The medicament for or method of neuroprotection may be of use in the treatment of subjects who are suffering from or at risk from a neurodegenerative disorder, such as a movement disorder.

The present invention may be employed in respect of a human or animal subject, more preferably a mammal, more preferably a human subject.

The disorders of particular interest are Parkinson's disease, drug-induced Parkinsonism, post-encephalitic Parkinsonism, Parkinsonism induced by poisoning (for example MPTP, manganese, carbon monoxide) and post-traumatic Parkinson's disease (punch-drunk syndrome).

Other movement disorders in which the therapy may be of benefit include progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spasticity, Alzheimer's disease or other disorders of the basal ganglia which result in abnormal movement or posture.

A further example of a disorder in which the blocking of purine receptors may be beneficial is depression.

(−)-(11S,2'R)-α-2-piperidinyl-2,8-bis(trifluoromethyl)-4-quinolinemethanol may be in the form of a mixture with (+)-(11R,2'S)-α-2-piperidinyl-2,8-bis(trifluoromethyl)-4-quinolinemethanol, or a pharmaceutically acceptable salt thereof. For example, the racemic mixture (±)-(R*,S*)-α-2-piperidinyl-2,8-bis(trifluoromethyl)-4-quinolinemethanol may be used.

(−)-(11S,2'R)-α-2-piperidinyl-2,8-bis(trifluoromethyl)-4-quinolinemethanol may be used or administered in combination with a second drug useful in the treatment of movement disorders, such as L-DOPA, the components being in the same formulation or in separate formulations for administration simultaneously or sequentially.

The present invention may also be effective in treating Parkinson's with on-off phenomena; Parkinson's with freezing (end of dose deterioration); and Parkinson's with prominent dyskinesias.

The pharmaceutical compositions employed in the present invention comprise (−)-(11S,2'R)-α-2-piperidinyl-2,8-bis(trifluoromethyl)-4-quinolinemethanol or mixtures thereof with (+)-(11R,2'S)-α-2-piperidinyl-2,8-bis(trifluoromethyl)-4-quinolinemethanol, or pharmaceutically acceptable salts thereof, and may also contain a pharmaceutically acceptable carrier and optionally other therapeutic ingredients known to those skilled in the art. The term "pharmaceutically acceptable salts", refers to salts prepared from pharmaceutically acceptable non-toxic acids including inorganic acids and organic acids.

Since the compounds employed in the present invention are basic, salts may be prepared from pharmaceutically acceptable non-toxic acids including inorganic and organic acids. Such acids include acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, and sulfuric acids, and most particularly preferred is the hydrochloride salt.

Any suitable route of administration may be employed for providing the patient with an effective dosage of (−)-(11S,2'R)-α-2-piperidinyl-2,8-bis(trifluoromethyl)-4-quinolinemethanol. For example, oral, rectal, parenteral (intravenous, intramuscular), transdermal, subcutaneous, and the like may be employed. Dosage forms include tablets, troches, dispersions, suspensions, solutions, capsules, patches, and the like. The most suitable route in any given case will depend on the severity of the condition being treated. The most preferred route of administration of the present invention is the oral route. The compositions may be conveniently presented in unit dosage form and prepared by any of the methods well known in the art of pharmacy.

In practical use, (−)-(11S,2'R)-α-2-piperidinyl-2,8-bis(trifluoromethyl)-4-quinolinemethanol can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. The most preferred solid oral preparation is tablets.

Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; 3,630,200; 4,008,719; 4,687,660; and 4,769,027, the disclosures of which are hereby incorporated by reference.

Pharmaceutical compositions employed in the present invention suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

The invention is further defined by reference to the following examples. It will be apparent to those skilled in the art that many modifications, both to materials and methods, may be practised without departing from the purpose and interest of this invention.

BRIEF DESCRIPTION OF THE DRAWINGS

FIG. 3 shows binding of the Mefloquine (+)- and (−)-enantiomers to human recombinant (HEK-293) adenosine $A_{2A}$ receptors (displacement of [$^3$H]-CGS 21680, an adenosine $A_{2A}$ receptor agonist).

FIG. 4 shows binding of the Mefloquine (+)- and (−)-enantiomers to human recombinant (HEK-293) adenosine $A_3$ receptors (displacement of [$^{125}$I]AB-MECA, an adenosine $A_3$ receptor agonist).

EXAMPLES

Preparation of 2,8-bis(trifluoromethyl)quinoline-4-carboxylic Acid

Figure 1:
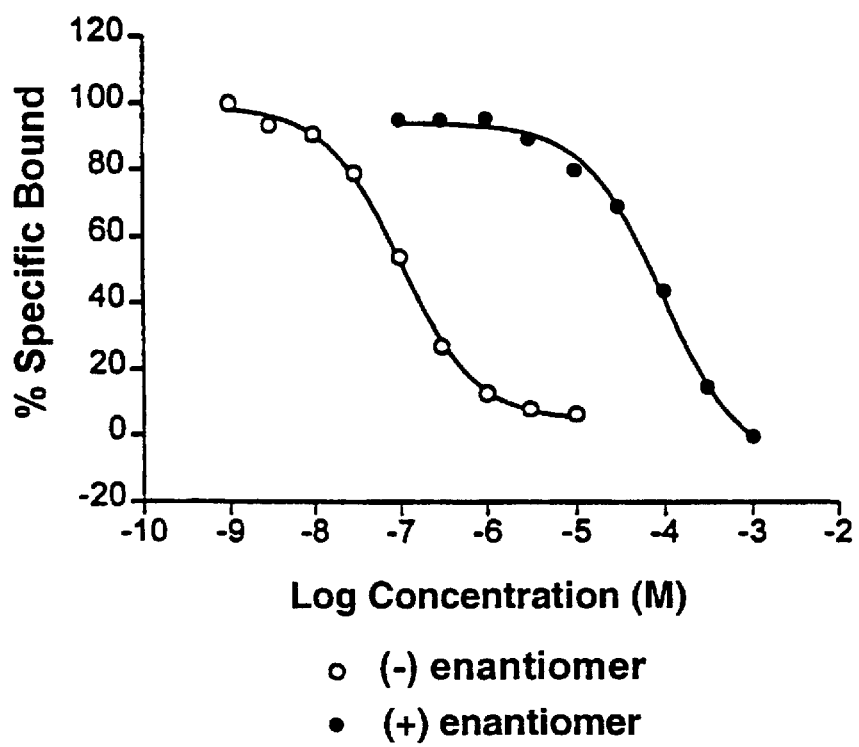
FIG. 1 shows binding of the Mefloquine (+)-enantiomer and (−)-enantiomer to bovine striatal adenosine (non-selective) receptors (displacement of the non-selective $P_1$ receptor ligand [$^3$H]-NECA ([$^3$H]-5'-N-ethylcarboxamidoadenosine)). Table 2 displays comparative data for the control compound MECA (5'-N-methylcarboxamidoadenosine).

The compound 2,8-bis(trifluoromethyl)quinoline-4-carboxylic acid was prepared by the method of Hickmann et al (U.S. Pat. No. 4,327,215).

Preparation of N-methoxy-N-methyl-2,8-bis(trifluoromethyl)-quinoline-4-carboxamide This compound was prepared using synthetic methodology reported by Thiesen et al (*J. Org. Chem.* 1988, 53, 2374). To a suspension of 2,8-bis(trifluoromethyl)quinoline-4-carboxylic acid (12.5 g, 40.4 mmol) in $CH_2Cl_2$ (200 ml) was added 1,1'-carbonyldiimidazole (7.3 g, 45 mmol) and N,O-dimethylhydroxylamine hydrochloride (4.25 g, 45 mmol). The resulting deep red solution was stirred overnight, then poured into dilute hydrochloric acid (0.25 M, 200 ml). The organic phase was separated, and washed in turn with dilute sodium hydroxide and brine, and dried ($MgSO_4$). The solvents was evaporated to leave a viscous brown oil, which was filtered through a pad of silica gel using ethyl acetate-hexane (1:1) as eluent to give a yellowish oil, 14.3 g (98%), which solidified on standing. This material was broken up under hexane to afford the product as a tan solid, m.p. 93–95° C. $\delta_H$ (400 MHz, CDCl$_3$) 8.22 (1H, d, J=1.5 Hz), 8.16 (1H, d, J=1.8 Hz), 7.85 (1H, s), 7.73 (t, J=1.2 Hz), 3.52 (3H, bs) and 3.41 (3H, bs). Analysis of this material by HPLC showed it to be >99.8% pure.

Preparation of Pyridin-2-yl-2,8-bis(trifluoromethyl)-quinoline-4-yl Ketone

To a solution of the amide described above (10 g, 28.4 mmol) in anhydrous ether (100 ml) was added a solution of 2-pyridyl lithium (Pinder et al (*J. Med. Chem.* 1968, 11, 267)) [formed by addition of 2-bromopyridine (3.3 ml, 34.6 mmol) to a solution of butyl lithium (29.7 ml of a commercial 1.6 M solution, diluted with an equal quantity of ether) at −78° C.] at −78° C. Analysis of the reaction by TLC after 10 min showed that no starting material remained. The reaction was allowed to warm to room temperature, then poured into aqueous ammonium acetate, and extracted with ether (2×100 ml), the combined organic layers washed with brine and dried ($MgSO_4$). Filtration through a pad of silica gel using ethyl acetate-hexane (1:1) afforded 9.0 g (84%) of the crude product. This was recrystallised from isopropyl alcohol to give the product as colourless needles, identical to that described in the literature (Hickmann et al; Pinder et al; Ohnmacht et al; and Adam et al. (*Tetrahedron* 1991, 36, 7609)).

Preparation of (R*,S*)-(±)-α-2-piperidinyl-2,8-bis(trifluoromethyl)-4-quinolinemethanol (Mefloquine)

This compound was prepared according to the literature procedure (Hickmann et al; Pinder et al; and Ohnmacht et al)

to give an 85:15 mix of the erythro:threo isomers (HPLC). Recrystallisation of the crude material from acetonitrile afforded the erythro isomer as a powdery white solid in >98% purity (HPLC).

Resolution of erythro enantiomers was performed according to the known procedure (Carrol, F. I. and Blackwell, J. T., J. Med. Chem. 1974, 17, 210–219).

Adenosine Receptor Interaction

The Mefloquine (+)- and (−)-enantiomers were initially examined separately in an assay measuring in vitro binding to adenosine receptors by determining the displacement of [$^3$H]-NECA binding to rat striatal membranes. The data are shown in FIG. 1 and Table 2.

TABLE 2

Binding of the Mefloquine (+)- and (−)- enantiomers to bovine striatal adenosine receptors (displacement of [$^3$H]-NECA). MECA is shown as control.

|  | $K_i$ |
|---|---|
| MECA | 58 nM |
| (+) enantiomer | 38 μM |
| (−) enantiomer | 83 nM |

Figure 2:
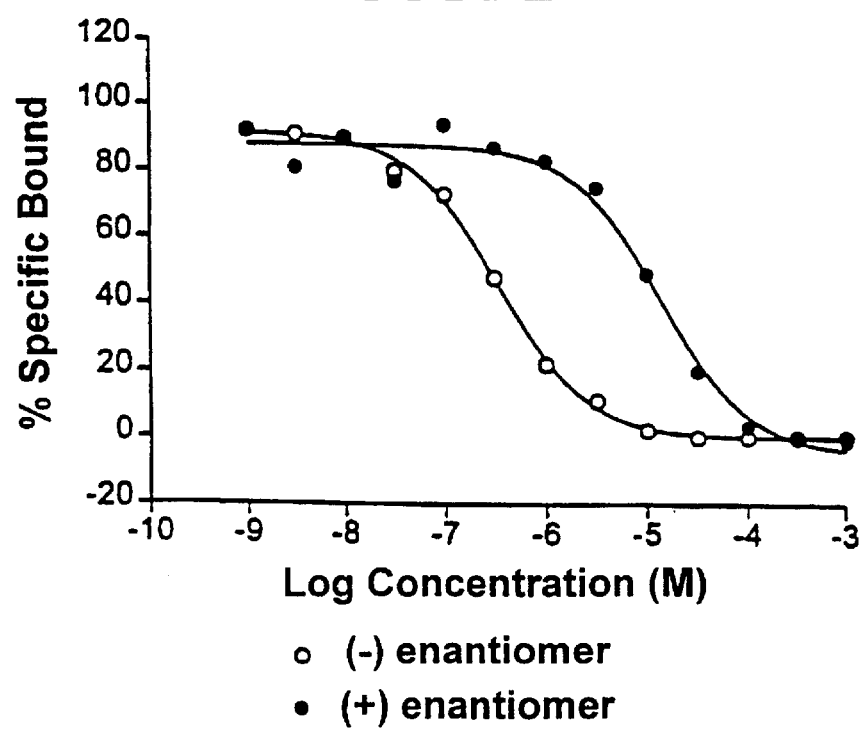
FIG. 2 shows binding of the Mefloquine (+)- and (−)-enantiomers to rat brain adenosine $A_1$ receptors (displacement of [$^3$H]-DPCPX, an adenosine $A_1$ receptor antagonist).

Once it was established that the (−)-enantiomer of mefloquine exhibited displacement of [$^3$H]-NECA in bovine striatum, the adenosine receptor subtype binding was examined using radioligand binding assays employing the selective $P_1$ radioligands [$^3$H]-DPCPX (adenosine $A_1$ receptor), [$^3$H]-CGS 21680 (adenosine $A_{2A}$ receptor) and [$^{125}$I]AB-MECA (adenosine $A_3$ receptor). The results are summarised in Table 3, with comparative literature data for other adenosine receptor ligands. The full dose response curves are shown in FIGS. 2–4.

TABLE 3

Binding of Mefloquine (+)- and (−)- enantiomers to adenosine $A_1$, $A_{2A}$ and $A_3$ receptors

BINDING ASSAY CONDITIONS

|  | Adenosine $A_1$ | Adenosine $A_{2A}$ | Adenosine $A_3$ |
|---|---|---|---|
| Source | Rat Brain | Human | Human |
| Ligand | 0.14 nM [$^3$H]-DPCPX | 4.0 nM [$^3$H]-CGS 21680 | 0.4 nM [$^{125}$I]AB-MECA |
| Non-Specific | 10 μM PIA | 10 μM NECA | 10 μM NECA |
| RESULTS ($K_i$) |  |  |  |
| (+) enantiomer | 6.4 μM | 1.8 μM | 7.7 μM |
| (−) enantiomer | 202 nM | 4.4 nM | 6.8 μM |
| Reference Adenosine receptor agonists |  |  |  |
| NECA | 17 nM | 19 nM | 110 nM |
| CHA | 26 nM | 510 nM | 7700 nM |
| Reference Adenosine $A_{2A}$ receptor antagonists |  |  |  |
| KW-6002† | 580 nM | 13 nM | na |
| KF17837† | 390 nM | 8 nM | Na |
| ZM241385‡ | 2.0 μM | 0.3 nM | 151 μM |

†Shimada et al., BioMed. Chem. Lett., 1997, 7, 2349–2352.
‡Poucher et al., Br. J. Pharm., 1995, 115: 1096–1102

The results of further experiments to examine the adenosine receptor subtype binding activity of the (−)-enantiomer of Mefloquine are shown in Table 4.

TABLE 4

Human adenosine receptor binding

|  | $K_i$/nM |
|---|---|
| Tissue/Cell: $hA_1$ (CHO-K1) |  |
| Radioligand: [$^3$H]-DPCPX |  |
| Mefloquine (−) enantiomer | 268 |
| ZM 241385 | 372 |
| DPCPX | 5 |
| THEOPHYLLINE | 11489 |
| CGS 21680 | 37691 |
| Tissue/Cell: $hA_{2A}$ (HEK-293) |  |
| Radioligand: [$^3$H]-CGS 21680 |  |
| Mefloquine (−)-enantiomer | 41 |
| ZM 241385 | 3 |
| DPCPX | 488 |
| THEOPHYLLINE | 3466 |
| CGS 21680 | 23 |

The above data lead to the conclusion that the mefloquine (−)-enantiomer is a ligand for the adenosine $A_{2A}$ receptor subtype in vitro. The binding of the (+)-enantiomer is over two orders of magnitude weaker.

Assessment of the Interaction of the (+)-enantiomer and the (−)-enantiomer with NECA in PC-12 Cells PC-12 cells (purchased from ECACC) were maintained in RPMI 1640 media (Sigma) supplemented with 2 mM L-glutamine and 10% FCS in a controlled environment of 5% $CO_2$, 95% humidity at 37° C.

On the day of the assay the cells were gently harvested and centrifuged at 700 RPM for 10 min. The supernatant was discarded and the pellet re-suspended to a final density of $1 \times 10^6$ cells/ml in RPMI 1640 media. 600 ml of this suspension was mixed with 200 ml of molten agarose cell entrapment media (Molecular Devices) pre-incubated to 37° C. The cell suspension was returned to the incubator for a further 10 minutes for equilibration. 10 ml of this cell agarose suspension was spotted onto the middle of the capsule insert well and allowed to set before being placed in the sensor chambers in the cytosensor® microphysiometer. The cells were maintained on the instrument with a low buffering capacity modified RPMI 1640 media (Molecular Devices) and their base line extracellular acidification rates allowed to settle.

Agonist concentration curves were constructed by exposing the cells in increasing concentrations of agonists for a total exposure time of approximately 1 min 53 sec. Agonist concentration curves in the presence of antagonists were performed following pre-incubation of the cells to the antagonists for at least 20 min prior to agonist exposure (in the presence of the fixed antagonist concentration). Baseline acidification rates were normalised to 100%, and all responses were calculated as a % increase over normalised baseline.

All data was fitted to Log-concentration response curves to calculate half maximally effective concentrations ($EC_{50}$ values) by non-linear regression using the Graph Pad Prism software package.

Figure 5:
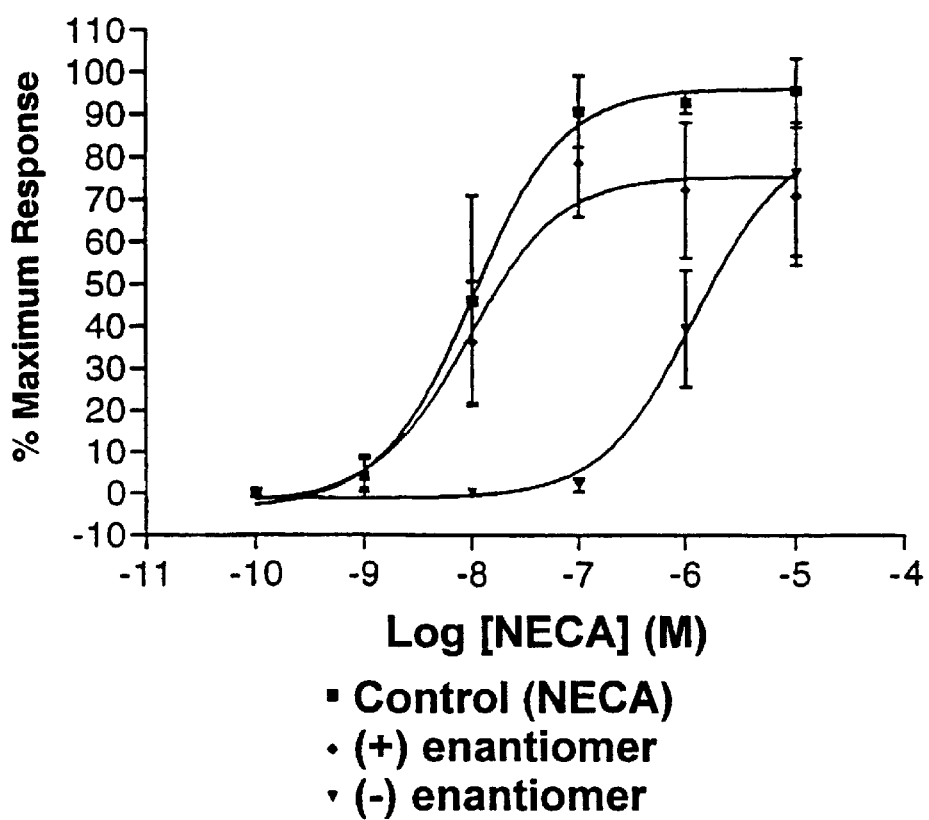
FIG. 5 shows the effect of the Mefloquine (+)- and (−)-enantiomers on the NECA-induced increase in extracellular acidification rate (ECAR) in PC-12 cells.

The results (shown in FIG. 5) indicate that the (−)-enantiomer, (−)-(11S,2'R)-α-2-piperidinyl-2,8-bis (trifluoromethyl)-4-quinolinemethanol, binds to adenosine receptors as an antagonist. PC12 cells express inter alia adenosine $A_{2A}$ receptors.

Effect of Mefloquine (+− and (−)-enantiomers on mouse striatal and frontal cortex neurochemistry 24 hours after drug administration.

Vehicle (1.0 ml/kg 0.3% hydroxypropylmethylcellulose suspension, p.o.), mefloquine (+)-enantiomer (100 mg/kg, p.o.) or mefloquine (−)-enantiomer (100 mg/kg, p.o.) was administered to female T.O. mice (300–350 g). 24 Hours later, the animals were killed and frontal cortex as well as striatum were dissected from the brain on ice. Tissue samples were frozen, and stored at −80° C. prior to analysis. An extraction procedure was utilised, described as follows: 10 volumes of perchloric acid were added to samples which were then homogenised and centrifuged (10,000 rpm, 10 min). Supernatant was collected (100 μl) and filtered (centrifuged through 0.45 μm Acrodisc mini-filters) ready for high performance liquid chromatographpy (HPLC) analysis. Striatal and frontal cortical tissue was assessed for the following components: dopamine, it metabolites 3,4-dihydroxyphenylacetic acid and homovanillic acid, 5-hydroxytryptamine and its metabolite 5-hydroxyindoleacetic acid on one HPLC system (electrochemical detection; carbon cell set to 0.65 V vs reference) and for acetylcholine on a second HPLC system (electrochemical detection of $H_2O_2$, resulting from post-column enzymic degradation of acetylcholine and choline by acetylcholinesterase and choline oxidase, respectively).

Figure 6:
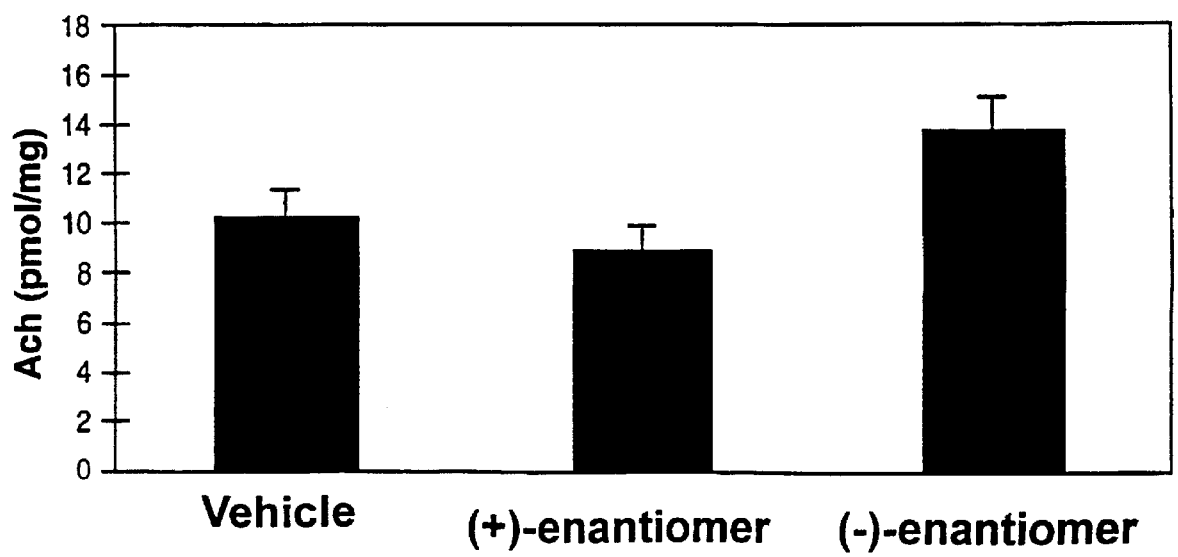
FIG. 6 shows the effect of the Mefloquine (+)- and (−)-enantiomer, dosed at 100 mg/kg p.o. in hydroxypropylmethylcellulose vehicle, on rat striatal acetylcholine content.

No significant difference was observed between mefloquine (+)-enantiomer or (−)-enantiomer on dopamine or 5-HT neurochemistry, nor on the transmitter metabolites. In contrast, striatal acetylcholine content was significantly higher in mice given the (−)-enantiomer as compared to those given the (+)-enantiomer (FIG. 6). Analysis of variance revealed a significant treatment affect; post-hoc Duncan's New Multiple Range tests revealed a significant difference between vehicle and the (−)-enantiomer ($p<0.05$), and between the (+)-enantiomer and the (−)-enantiomer ($p<0.01$). Frontal cortex acetylcholine was unaffected by either enantiomer.

An increase in brain tissue acetylcholine content is generally considered to be indicative of a decrease in the synaptic release of the neurotransmitter. Thus, a dopamine $D_2$ receptor agonist, such as quinpirole, is known to attenuate the in vivo release of striatal acetylcholine (DeBoer, P. and Abercrombie, E. D. Physiological release of striatal acetylcholine in vivo: modulation by $D_1$ and $D_2$ dopamine receptor subtypes. *J. Pharmacol. Exp. Ther.* 1996, 277, 775–783; Bickerdike, M. J. and Abercrombie, E. D. Striatal acetylcholine release correlates with behavioral sensitization in rats withdrawn from chronic amphetamine. *J. Pharmacol. Exp. Ther.* 1997, 282: 818–826), but produces an increase in ex vivo striatum acetylcholine content (Forloni, G. et al., Striatal cholinergic function reflects differences in D-2 dopaminergic receptor activation. *Life Sci.* 1987, 41, 1717–23).

The results shown in FIG. 6 therefore suggest that the mefloquine (−)-enantiomer, (−)-(11S,2'R)-α-2-piperidinyl-2,8-bis(trifluoromethyl)-4-quinolinemethanol inhibits acetylcholine release in striatum. This is consistent with the binding data generated for this (−)-enantiomer, indicating that it has affinity for the adenosine $A_{2A}$ receptor. Adenosine $A_{2A}$ receptor antagonism has been demonstrated in separate studies to result in diminished striatal acetylcholine release (Richardson, P. J. et al., Adenosine $A_{2A}$ receptor antagonists as new agents for the Treatment of Parkinson's disease. *Trends Pharmacol. Sci.* 1997, 18, 338–344).

This effect on acetylcholine release has been suggested to be one of a number of important mechanisms by which adenosine $A_{2A}$ receptor antagonists, such as the mefloquine (−)-enantiomer, exert anti-Parkinsonian effects.

Evaluation of Potential Anti-Parkinsonian Activity in vivo Haloperidol-induced Catalepsy in the Rat This method assessed the ability of an animal to respond to an externally imposed posture after receiving the neuroleptic dopamine $D_2$ antagonist haloperidol. Drugs which are effective in treating Parkinson's disease, such as L-DOPA, block haloperidol-induced catalepsy (Mandhane, S. N.; Chopde, C. T.; Ghosh, A. K. (1997). Adenosine $A_2$ receptors modulate haloperidol-induced catalepsy in rats. *Eur. J. Pharmacol.*, 328, 135–141).

The (−)-enantiomer of mefloquine (0, 0.1, 1, 10 mg/kg) was suspended in a 0.3% solution of hydroxypropylmethylcellulose (HPMC)/saline. Haloperidol (0.2 mg/kg) was obtained in injectable form and diluted to a final concentration using physiological saline. 3,7-Dimethyl-1-propargylxanthine (DMPX) (0, 3 mg/kg) was dissolved in saline. All drugs were administered in a volume of 2 ml/kg. Animals received three injections: (1) vehicle or (−)-enantiomer of mefloquine (0.1–10 mg/kg) p.o. 6 hours prior to testing, (2) haloperidol (0.2 mg/kg) i.p. 2.5 hours prior to testing, and (3) vehicle or DMPX (3 mg/kg) 30 minutes prior to testing.

The test procedure was as follows:

Step I The rat was taken out of the home cage and placed on a table. If the rat failed to move when touched gently on the back or pushed, a score of 0.5 was assigned.

Step II The front paws of the rat were placed alternately on a 3 cm high wooden block. If the rat failed to correct this posture within 15 s, a score of 0.5 for each paw was added to the score of Step I.

Step III The front paws of the rat were placed alternately on a 9 cm high wooden block. If the rat failed to correct the posture within 15 s, a score was added to the scores of Step I and II. Thus for any animal the highest score obtainable was 3.5 (cut-off score) reflecting total catalepsy.

Figure 7:
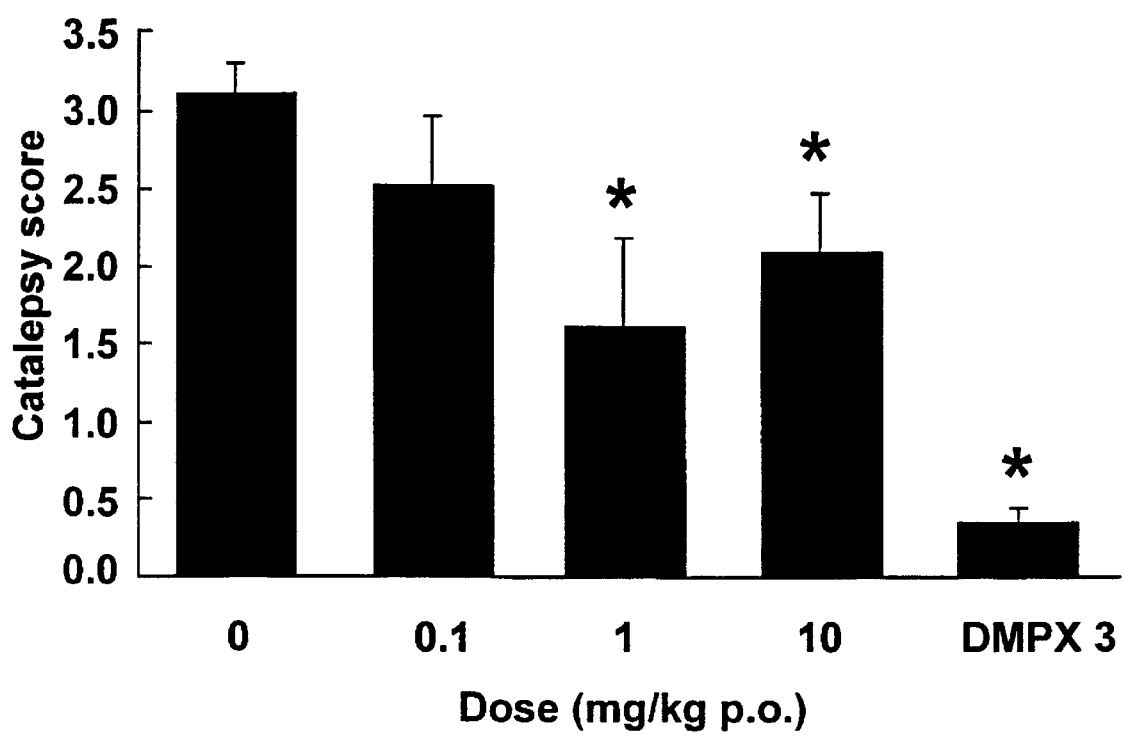
FIG. 7 shows the effect of the Mefloquine (−)-enantiomer on haloperidol-induced catalepsy.

Data from the experiment were analysed using Kruskal-Wallis ANOVA followed by Mann-Whitney U test when appropriate, and are expressed as means +/− standard error of the mean $*p<0.05$ versus vehicle control. The results are displayed graphically in FIG. 7. The results indicate that the (−)-enantiomer of Mefloquine is capable of blocking haloperidol-induced catalepsy.

MPTP Lesion Model

Mice (C57/BL Harlan) received a unilateral intrastriatal injection of the test compound, vehicle control, and positive control, in a volume of 1.0 μl (15 mice per group). 30 min. after administration of the test compound all mice were systemically administered MPTP (N-methyl-4-phenyl-1,2,5,6-tetrahydropyridine) (25 mg/kg s.c), and this MPTP treatment was repeated 24 hours later. At suitable time points the spontaneous locomotor activity of the animals, as measured in automated activity monitors, was compared with control animals. Animals was sacrificed 14 days after the second MPTP injection and striatal tissue was dissected out for HPLC analysis of dopamine and its metabolites, 3,4-dihydroxyphenylacetic acid and homovanillic acid. Reverse-phase HPLC in conjunction will electrochemical detection (Antec Decade detector, glossy carbon cell, set to +0.65 V versus a Ag/AgCl reference) was employed. The HPLC mobile phase consisted of 0.15 M $NaH_2PO_4$, 0.1 mM EDTA, 0.55 mM octyl sulphate, 16% methanol (pH 3.6, adjusted with orthophosphoric acid). The effects of test compounds on MPTP-induced mesencephalic damage was demonstrated by comparison with dopamine, 3,4-dihydroxyphenylacetic acid and homovanillic acid levels in caudate tissue taken ipsilateral and controlateral to the test compound injection. The influence of test compounds on MPTP-induced effects on locomotion and catecholamine and metabolite tissue levels were assessed by repeated measures analysis of variance (ANOVA) with appropriate post-hoc tests.

What is claimed is:

1. A method of treating or preventing a disorder in which the blocking of purine receptors may be beneficial, comprising administering to a subject in need of such treatment an effective dose of (−)-(11S,2'R)-α-2-piperidinyl-2,8-bis(trifluoromethyl)-4-quinolinemethanol or a pharmaceutically acceptable salt thereof.

2. A method according to claim 1, wherein said disorder is caused by the hyperfunctioning of purine receptors.

3. A method according to claim 2, wherein said pruine receptors are adenosine receptors.

4. A method according to claim 3, wherein said adenosine receptors are $A_{2A}$ receptors.

5. A method of treating or preventing movement disorders, comprising administering to a subject in need of such treatment an effective dose of (−)-(11S,2'R)-α-2-piperidinyl-2,8-bis(trifluoromethyl)-4-quinolinemethanol or a pharmaceutically acceptable salt thereof.

6. A method according to claim 5, wherein said subject is human.

7. A method according to claim 5, wherein said movement disorder is Parkinson's disease.

8. A method according to claim 7, for treatment of drug-induced Parkinsonism, post-encephalitic Parkinsonism, Parkinsonism induced by poisoning or post-traumatic Parkinson's disease.

9. A method according to claim 5, wherein said movement disorder is selected from the group consisting of progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spacticity, Alzheimer's disease and other disorders of the basal ganglia which result is dyskinesias.

10. A method according to claim 5, wherein (−)-(11S,2'R)-α-2-piperidinyl-2,8-bis(trifluoromethyl)-4-quinolinemethanol is in combination with a second drug useful in the treatment of movement disorders, the components being in the same formulation or in separate formulations for administration simultaneously or sequentially.

11. A method according to claim 10, wherein said movement disorder is Parkinson's disease.

12. A method according to claim 11, wherein said second drug is L-DOPA.

13. A method according to claim 1, wherein said disorder is depression.

14. A method of neuroprotection, comprising administering to a subject in need of such treatment an effective dose of (−)-(11S,2'R)-α-2-piperidinyl-2,8-bis(trifluoromethyl)-4-quinolinemethanol or a pharmaceutically acceptable salt thereof.

15. A method according to claim 14, wherein said method is for neuroprotection in a subject suffering from or at risk from a neurodegenerative disorder.

16. A method according to claim 15, wherein said neurodegenerative disorder is a movement disorder.

17. A method according to claim 16, wherein said movement disorder is Parkinson's disease.

18. A method according to claim 1, wherein said (−)-(11S,2'R)-α-2-piperidinyl-2,8-bis(trifluoromethyl)-4-quinolinemethanol is in the form of a mixture with (+)-(11R,2'S)-α-2-piperidinyl-2,8-bis(trifluoromethyl)-4-quinolinemethanol or a pharmaceutically acceptable salt thereof.

19. A method according to claim 18, wherein said mixture is a racemic mixture.

20. A method according to claim 17, for treatment of drug-induced Parkinsonism, post-encephalitic Parkinsonism, Parkinsonism induced by poisoning or post-traumatic Parkinson's disease.

21. A method according to claim 16, wherein said movement disorder is selected from the group consisting of progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spasticity, Alzheimer's disease and other disorders of the basal ganglia which result is dyskinesias.

22. A method according to claim 5, wherein said (−)-(11S,2'R)-α-2-piperidinyl-2,8-bis(trifluoromethyl)-4-quinolinemethanol is in the form of a mixture with (+)-(11R,2'S)α-2-piperidinyl-2,8-bis(trifluoromethyl)-4-quinolinemethanol or a pharmaceutically acceptable salt thereof.

23. A method according to claim 22, wherein said mixture is a racemic mixture.

24. A method according to claim 14, wherein said (−)-(11S,2'R)-α-2-piperidinyl-2,8-bis(trifluoromethyl)-4-quinolinemethanol is in the form of a mixture with (+)-(11R,2'S)α-2-piperidinyl-2,8-bis(trifluoromethyl)-4-quinolinemethanol or a pharmaceutically acceptable salt thereof.

25. A method according to claim 24, wherein said mixture is a racemic mixture.

* * * * *